United States Patent [19]

Enger

[11] 4,319,578
[45] Mar. 16, 1982

[54] MICRO PH ELECTRODE ASSEMBLY FOR WIRE TRANSMISSION

[75] Inventor: Carl C. Enger, Lakewood, Ohio

[73] Assignee: General Mills, Inc., Minneapolis, Minn.

[21] Appl. No.: 82,448

[22] Filed: Oct. 9, 1979

[51] Int. Cl.³ .............................................. A61B 5/00
[52] U.S. Cl. .................................................. 128/635
[58] Field of Search ..................... 128/635; 204/195 B

[56] References Cited

U.S. PATENT DOCUMENTS

| | | | |
|---|---|---|---|
| 3,224,433 | 12/1965 | Von Palebor | 128/635 |
| 3,259,124 | 7/1966 | Hillier et al. | 128/635 |
| 4,207,146 | 6/1980 | Kunke | 128/635 |

OTHER PUBLICATIONS

Newman et al., "Archives of Oral Biology", vol. 24, 1979, pp. 501–507.
Graf et al., "Helvetica Odontologica Acta", vol. 15, 1971, pp. 42–50.
Imfeld, "Helvetica Odontologica Acta", vol. 21, May 1977, pp. 1–28.
"Telemetry of Plaque pH from Interdental Plaque" by H. Graf and H. R. Muhlemann, *Helvetica Odontologica Acta*, vol. 10, 94–102 (Oct. 1966).
"Effects of Carbohydrate Restriction in Monkeys (M.irus) with Active Caries" by W. H. Bowen and Diana E. Cornick, *Helvetica Odontologica Acta*, pp. 27–31 (Apr. 1967).

*Primary Examiner*—William E. Kamm
*Attorney, Agent, or Firm*—Gene O. Enockson; John A. O'Toole

[57] ABSTRACT

Miniature pH indicator electrode assemblies (e.g., 10 mm. length) are provided for wire transmission. Also provided are dental assemblies containing such pH indicator electrode assemblies. The pH indicator electrode assemblies comprise micro pH indicator electrodes, wire transmission connector plugs, and heat shrinkable plastic housings. A moisture and ion impermeate, plastic seal intermediate the housing and both the electrode and the plug prevents moisture penetration therein. Dental assemblies containing such pH electrode assemblies are useful for the continuous measurement by wire transmission of pH changes in oral cavity fluids at both specific and non-specific sites.

30 Claims, 6 Drawing Figures

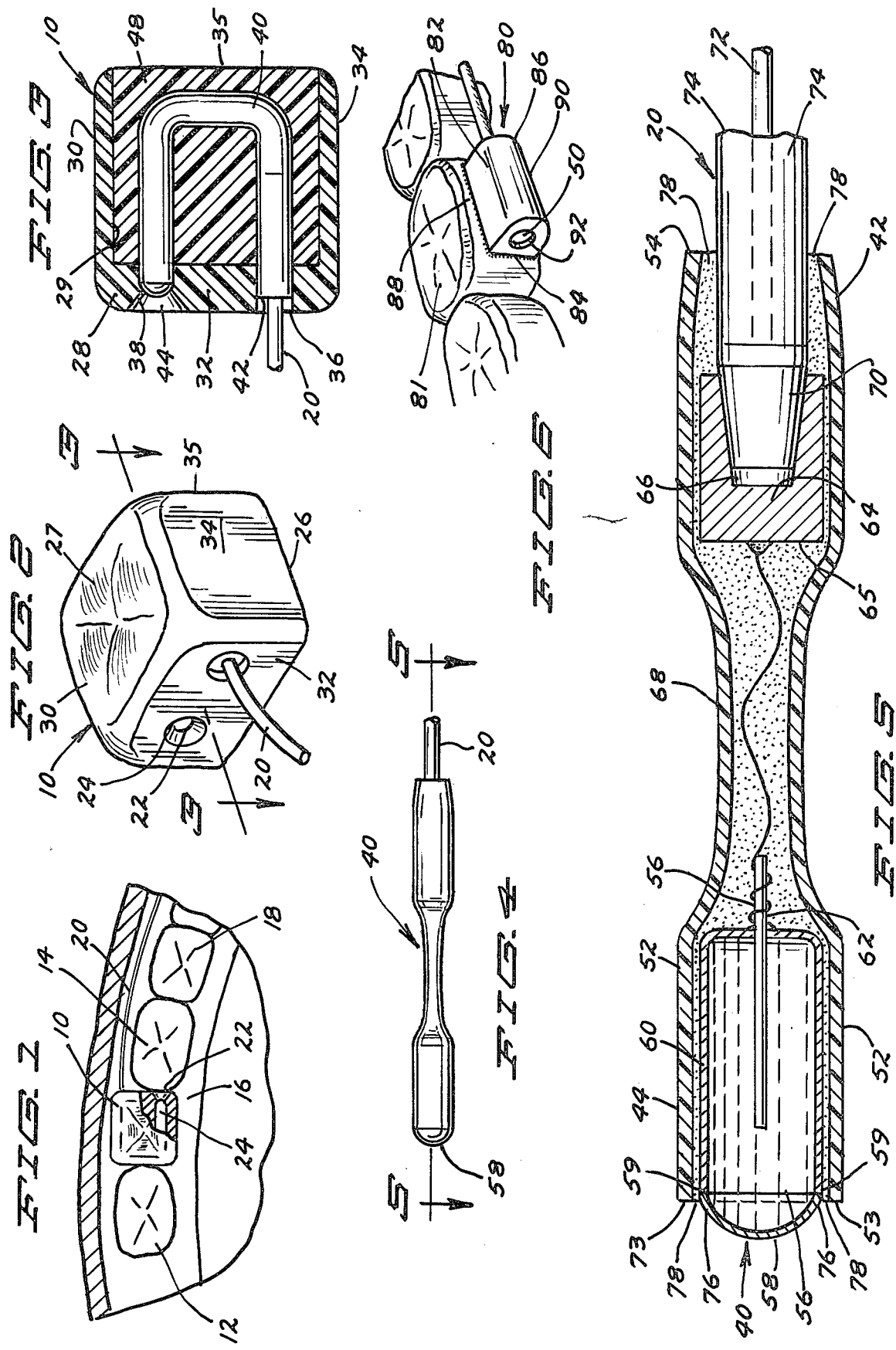

MICRO PH ELECTRODE ASSEMBLY FOR WIRE TRANSMISSION

BACKGROUND OF THE INVENTION

1. Field of the Invention

This invention relates to micro pH electrode assemblies for wire transmission. More particularly, this invention relates to micro pH electrode assemblies which are specially adapted for use to continuously measure by wire transmission changes in the pH of fluids in the oral cavity and to dental assemblies housing such electrodes.

2. The Prior Art

Dental research has recognized a close interrelation between dental plaque and tooth decay. It is generally accepted that dental caries are produced by the decalcification of the teeth by acids liberated by acidogenic bacteria associated with the dental plaque. Dietary sugars are readily metabolized by these acidogenic bacteria. The generation of acids starts almost immediately after food consumption.

While studies of changes in the pH of oral cavity fluids occurring after consumption of foodstuffs could indicate such foodstuffs' cariogenic potential, such measurements presently are taken only with great difficulty. One problem presented is to directly, continuously and accurately measure the particular biological phenomenon without disturbing the process to be evaluated. Wire transmission pH electrode apparatus have been used in the past with some success to measure both gross and in situ changes in the pH of oral cavity fluids (see "Evaluation of the Cariogenicity of Confectionary in Intra-Oral Wire Telemetry" by T. Imfeld, *Helvetica Odontologica Acta* 21, 1:1-28 (1977).

Such measurement apparatus, are, however, subject to serious limitations. The apparatus which has been used in the past generally required the space of several removed teeth from the upper and lower jaws. The apparatus is thus relatively large, difficult to wear for extended periods, and therefore can be used only with a relatively small number of potential subjects. In contrast, the reduced size, false tooth or "pontic" dental assemblies of the present invention housing the present micro pH electrode assemblies can fit into the space of only a single removed tooth. Indeed, the present "inpontic" dental assemblies (i.e., those not serving as a false tooth) can be used on subjects having a full set of natural teeth. Furthermore, due to their greatly reduced size, the present dental assemblies can be worn with comparative ease for the extended time periods necessary for the development of required bacterial plaque.

The development of micro pH indicator electrodes in the art was necessary to the development of the present dental apparatus. Such micro pH indicator electrodes are now commercially available. However, these micro pH indicator electrodes are delicate and fragile due to their small size. Thus, one problem in providing practical wire transmission assemblies employing such micro pH electrodes was the development of an appropriate flexible housing which both protected the delicate micro electrodes and also provided for wire transmission of the pH measurement. In the development of such a housing, unforeseen difficulties arose in constructing apparatus capable of continuous and accurate pH measurement. It was surprisingly discovered that moisture and ionic migration by, apparently, capillary action between the housing and both the micro electrode and the wire transmission connection plugs were responsible for short circuiting and for aberrant readings. The moisture and ionic migration problems were severely aggravated by the reduction in the size of the micro electrodes and the attendant need for close fitting protective housing. It has now been surprisingly discovered that the moisture and ionic migration can be prevented, and accurate and continuous micro indicator electrode pH assemblies can be constructed by providing a moisture and ion impermeable, plastic seal intermediate the micro electrode and its housing.

SUMMARY OF THE INVENTION

The present invention relates to miniaturized pH indicator electrode assemblies for wire transmission and to both pontic and inpontic dental assemblies housing them. The pH electrode assemblies are constructed such as to be sealed against ion and moisture penetration by capillary action. Such a construction thus provides for accurate pH measurement of on-going biological processes with reduced malfunction due to moisture short circuiting. Such articles are useful in the intra oral, wire transmission measurement of pH changes in oral cavity fluids.

BRIEF DESCRIPTION OF THE DRAWINGS

FIG. 1 is a partial top elevational view of the dental assembly of the present invention as used in the oral cavity;

FIG. 2 is an enlarged perspective view of the dental assembly;

FIG. 3 is a sectional view of the dental assembly taken along lines 3—3 of FIG. 2;

FIG. 4 is a top view of the wire transmission pH electrode assembly of the present invention;

FIG. 5 is an enlarged sectional view of the pH electrode assembly taken along lines 5—5 of FIG. 4;

FIG. 6 is a perspective view of another embodiment of the dental assembly.

DESCRIPTION OF THE PREFERRED EMBODIMENT

Referring now to the drawings, and particularly to FIG. 1 thereof, there is shown a dental assembly 10 of the present invention as it is to be used in the oral cavity. The dental assembly 10 is positioned between a third molar 12 and a first molar 14 each of which molars are positioned in the gingival tissue 16. The dental assembly 10 has been inserted into the space resulting from the removal of a second molar. It will be appreciated, however, that appropriately sized and shaped dental assemblies of the present invention could be inserted into the space formed by the removal or absence of any of the molars or bicuspids 18 whether maxillary (i.e., upper jaw) or mandibular (i.e., lower jaw).

Further depicted in FIG. 1 is the transmission wire 20 leading from the buccal or cheek side of the dental assembly 10. The transmission wire 20 leads to conventional recording and reference apparatus which are not a part of the present invention. There is further seen a flared aperture 22 in the dental assembly 10 in the mesial or forward interproximal (i.e., between adjacent teeth) surface proximate the first molar 14. The aperture allows contact between the sensing tip (described below) of a present pH electrode assembly designated generally by reference numeral 24, and interdental oral cavity fluids, not depicted, to continuously measure changes in the pH thereof.

In FIG. 1, the orientation of the dental assembly 10 is such that the aperture 22 is on the lingual or tongue side. It is to be appreciated, however, that the dental assembly can be so constructed and so oriented in the mouth such that the aperture 22 would be on the buccal or cheek side of the dental assembly. And too, the aperture could be on a distal or rearward interproximal surface of the dental assembly rather than the mesial or forward orientation depicted.

Reference now is made to FIG. 2, a greatly enlarged perspective view of the dental assembly 10. The dental assembly is generally cubular and has a bottom surface 26, a top or occlusal surface 27, and three side or facial walls 30, 32 and 34. As shown in FIG. 3, the fourth side 35 of the assembly 10 is open. These walls are referred to as "facial walls" since the dental assembly 10 can be shaped in the general configuration of a tooth and can function as a pontic. Thus, the edges of the dental assemby 10 can be rounded or beveled so as to provide a dental assembly which does not have sharp edges. In particular, the occlusal surface 27 of the dental assembly 10 can be shaped in the general configuration of a tooth occlusal surface to aid in the pontic function.

As seen more clearly in FIG. 3, the dental assembly 10 comprises a hollow dental assembly housing 28. The dental assembly housing 28 can be composed of conventional pontic composite materials. In one embodiment of the present invention, the dental assembly housing 28 is prepared by hollowing out a block of a ceramic material to form an enlarged interior cavity designated by reference numeral 29. Suitable ceramic materials are those which are machinable, which are inert to oral cavity fluids, and which are strong enough to withstand normal biting forces. An exemplary material of this type is MACOR ® which is a machinable ceramic sold by Corning Glass Works, Inc.

In FIG. 3, the dental assembly housing 28 has a facial wall 32 which is opposed to the open side 35 of the dental assembly housing 28. The facial wall 32 has a first bore or passageway 36 and a second bore or passageway 38. The second passageway 38 is depicted as having a flared portion proximate its exterior end. Such a flared portion or aperture aids contact between the sensing tip of the indicator electrode and fluids whose pH is to be measured.

A micro pH electrode assembly 40 of the present invention is depicted as having a U-shaped configuration, a wire end 42 and a sensing tip end 44. The pH electrode assembly 40 is positioned within the dental assembly housing such that the wire end 42 is mounted within the passageway 36 so that it is proximate the exterior end of the passageway 36, while the sensing tip end 44 is proximate the exterior flared end of the passageway 38.

It is to be noted that the facial wall 32 in the preferred embodiment is thicker than the pair of opposed facial walls 30 and 34. This construction allows the pH electrode assembly to be more securely positioned within the first and second passageways. In the preferred embodiment, the facial wall 32 is opposed to the open side of the dental assembly housing. This construction aids the fabrication of the present dental assemblies. It will be appreciated, however, that the thicker facial wall 32 is not necessarily opposed to the open side of the dental assembly housing. Thus, other dental assemblies can be constructed wherein either facial walls 30 and 34 are supplied with a pair of bores or passageways for mounting the U-shaped pH electrode assembly. In still another embodiment, two facial walls can be supplied with a single bore or passageway aligned with one another such that a straight pH electrode assembly is mounted within the passageways.

The cavity 29 of the dental assembly housing 28 can be filled with packing or filler 48 such as with epoxy, common dental cement, paraffin or beeswax. Low melting point materials such as beeswax and paraffin are preferred due to the ease with which the packing can be removed so as to allow replacement of the pH electrode assembly as needed. The filler or packing thus surrounds that portion of the pH electrode assembly 40 projecting inwardly into the cavity of the dental assembly housing and securely anchors the pH electrode assembly within the housing. The packing or filler 48 can be easily added to the cavity of the dental assembly housing through the open side 35 while soft, and thereafter being allowed to set or harden.

Referring now to FIG. 4, there is shown a straight, wire transmission, pH electrode assembly 40 of the present invention which is capable of being bent to form the U-shaped pH electrode assembly 40 of FIG. 3. In the fabrication of the present dental assembly the U-shaped pH electrode assembly 40 can be inserted into the dental assembly housing 28 through the open side 35 of the dental assembly housing and into the cavity 29 thereof. After the U-shaped pH electrode assembly has been suitably positioned within the first and second passageways 36 and 38 of sidewall 32 as described above, then the remainder of the cavity is filled with fresh dental cement which is allowed to harden as described above.

FIG. 5 is a greatly enlarged sectional view of a straight, wire transmission pH electrode assembly 40 taken along lines 5—5 of FIG. 4. The pH electrode assembly 40 comprises a flexible tubular housing 52 having an opposed pair of ends, 53 and 54, generally referred to as a first or sensing tip and a second or wire end, respectively. The housing is essentially composed of a flexible, heat shrinkable plastic tubing having an unshrunken inner diameter 30% to 100% greater than the diameter of the pH electrode 56. Such a housing material desirably shrinks upon heating (80° C.) to about 70% of its initial inner radial dimensions and remains permanently shrunken upon cooling. The radially inward mechanical pressure exerted by the housing material on the pH indicator electrode after having been shrunken mitigates the capillary action problem. Surprisingly, undersized elastic tubing, i.e., tubing whose inner diameter is less than the diameter of the pH indicator electrode, which has been stretched by insertion of the pH indicator electrode does not provide the requisite radially inward mechanical pressure for useful lengths of time. Thus, more is involved than merely providing a snug fit. While not wishing to be bound by the proposed theory, it is believed that simple elastic tubing gradually relaxes over time its radially inward pressure whereas the essential heat shrinkable tubing's pressure remains relatively uniform.

Thus, for example, when a 1 mm. diameter pH indicator electrode is to be housed, a plastic tubing having an unshrunken inner diameter of about 1.3 to 2.0 mm. can be employed. Unrestricted, such a housing would be heat shrinkable in its inner radial dimensions of about 70%, i.e., to shrunken inner diameters of about 0.4 to 0.6 mm. An exemplary heat shrinkable plastic tubing material is 1.5 mm. I.D. radiation catalyzed polyolefin manufactured by Alpha Wire Corp. Of course, that portion of the heat shrunken housing surrounding the pH electrode is prevented from constricting completely by virtue of the larger diameter of the indicator electrode thus causing the exertion of the essential inwardly radial mechanical pressure described supra. However,—as best seen in FIG. 5—that portion of the housing intermediate the pH indicator electrode 56 and the plug 64 is pinched or constricted, relatively, compared to the restrictedly shrunken portions surrounding the pH indicator electrode 56 and the plug 64. Such a pinched construction of the intermediate portion of the housing advantageously aids the fixedly positioning of both the pH indicator electrode 56 and the plug 64 within the housing 52.

In FIG. 5, a micro pH indicator electrode 56 is positioned within the housing such that the sensing tip of the electrode 58 is proximate the first end or sensing tip end 53 of the housing. The pH indicator electrode 56 is responsive to changes in hydrogen ion activity of solutions applied to it. Electrodes of this type are commercially available from Micro Electrodes, Inc. (Londonberry, N.H.) and desirably range in length from about 3 to 8 mm. and from about 1 mm. to 2 mm. in diameter. The pH indicator electrode is conventional in its structure and can be generally characterized as a glass container 60 of ionically conductive aqueous solutions. Bonded to the glass container 60 and forming a seam 59 therewith is a convex sensing tip 58 which is sensitive to changes in the hydrogen ion activity of solutions and thus the changes in the solutions ' electric potential. Changes in the electric potential of this sensing tip 58 are communicated through the ionic solution to the opposed electrode axial stem 62, which projects inwardly into the housing 52. The electrode stem 62 is typically composed of platinum or other electrically conductive material.

The electrode stem 62 of the pH indicator electrode 56 is electrically connected with a plug 64. In FIG. 5, the electrode stem is electrically connected to the plug with a first or "short" wire 68, e.g., 10 strand insulated platinum wire. The wire 68 can be wrapped around the electrode stem 62 and fixedly attached thereto such as by gluing with epoxy. Similarly, the wire 68 is electrically and fixedly connected to the plug's flat facing or head 65 such as by soldering. The wire 68 has some excess length compared to the distance between the stem 62 and the flat facing 65 so as to allow the pH electrode assembly to be bent without rupturing the electrical connection between the indicator electrode and the plug.

The plug 64 is generally a solid cylinder and is composed of an electrically conductive material. In the preferred embodiment, the plug is composed of gold alloys such as 18 k gold, although platinum, silver, copper or aluminum can also be used. As can be seen from FIG. 5, the electrically conductive plug 64 is positioned proximate the opposed second or wire end 54 of the pH electrode assembly housing 52. In a preferred embodiment, the plug 64 is recessed from the end 54 of the housing 52. In FIG. 5, the plug 64 is depicted as having an outwardly facing socket 66 adapted to receive a tapered or cone shaped connecting tip 70, although other configurations of socket and tip can be used. In addition to the connecting tip 70, the transmission wire 20 also comprises an electrically conductive second wire 72 surrounded by electrical insulation 74. The second wire 72 can be thicker than the short wire and desirably composed of the same electrically conductive material as the plug 64 and the connecting tip 70.

It is important that the pH indicator electrode 56 is sealed to the housing 52 against ionic migration and particularly against moisture migration or penetration. Similarly, it is equally important for the plug 64 to be similarly sealed to the housing. Penetration of moisture or various ions behond the seam 59 between the sensing tip 58 and the glass container 60 can severely interfere with the indicator electrode's ability to accurately and continuously measure pH changes. Moisture migration/penetration by capillary action is aggravated by the minute physical dimensions of the annular space between the pH indicator electrode 56 and the housing 52. Sealing problems are further aggravated by the small surface area of the glass container 60 due to the pH indicator electrode's small size. The less surface area available for sealing, the less is the likelihood of the sealing means interrupting passageways leading from the exterior of the pH electrode assembly. Similar problems arise from the small size of the plug 64.

To prevent the problems associated with moisture penetration, the present pH indicator electrode assembly 50 is provided with means for sealing the indicator electrode 56 and the plug 64 to the housing 52 against moisture migration. In the preferred embodiment, such sealing means comprise a sealing layer 78 which fills the annular space between the housing 52 and the pH indicator electrode 56. The sealant material can fill the entire region inside the tubular housing 52 intermediate the electrode 56 and the plug 64 as shown in FIG. 5. As can be seen in FIG. 5, the sealing layer 78 at the sensing tip end 53 of the pH electrode assembly desirably extends outwardly beyond the seam or connection 59 between the sensing tip 58 and the remainder of the glass container 60 of the pH indicator electrode. Such a construction aids the pH measurement accuracy of the present electrode assembly.

In the preferred embodiment, the sealing layer comprises a moisture and ion impermeable, hydrophobic, plastic, water-immiscible material such as petroleatum which is more commonly known as "petroleum jelly." When used with reference to the sealing material, the term "plastic" is used herein in its conventional usage to refer to materials which exhibit the rheological property of plasticity, i.e., experiencing permanent deformation when subjected to a stress exceeding the material's yield value. Other materials of this type such as synthetic waxes, or silicone stopcock grease can also be used. In the most preferred embodiment, impermion pastes are employed such as are described in U.S. Pat. No. 3,659,612 (issued May 2, 1972 to C. C. Enger) and U.S. Pat. No. 3,963,677 (issued June 15, 1976 to C. C. Enger), each of which is incorporated herein by reference.

In a typical manner of operation, a pontic dental assembly is first fixedly positioned into a space of a missing tooth. Such a placement can be made permanent such as by cementing or bonding to the adjoining teeth. Conventional dental acid-etch bonding can be used to accomplish such bonding. Alternatively such a placement can be temporary such as by utilizing a conventional dental bridge. The dental assembly is then worn for a sufficient period of time to form a layer of plaque. When a subject's regular regimen of oral hygiene practices is foregone, a suitable plaque layer readily develops within 2–14 days. After the plaque layer has developed, the dental assembly having the pH indicator electrode assembly 50 as a component thereof can be used to measure the changes in the pH of fluids in the dental plaque layer after consumption of foodstuffs.

In a typical testing proceduure, the connecting tip 70 of the transmission wire 20 is dipped in the sealant layer material and then is plugged into the wire end 42 of the pH indicator electrode assembly 56 to electrically connect with the plug 64. The transmission wire 20 is then electrically connected to a conventional pH meter equipped with a strip recorder. The electrical circuit is completed when the subject's body is in contact with a reference electrode or solution. For convenience, a conventional disposable EKG electrode (e.g., Har-155 manufactured by Harco Electronics, Ltd. of Canada) in electrical contact with the subject's skin can serve as the reference electrode. Thereafter, the subject is allowed to consume a foodstuff. Changes in the pH of the oral cavity fluids resulting from consumption of the foodstuff typically occur within 1–30 minutes and can be thus measured and recorded by wire transmission.

Referring now to FIG. 6, there is shown a perspective view of another embodiment of the present dental assemblies. In this embodiment, the dental assembly is adapted to be affixed to a facial surface of an existing tooth designated by the reference numeral 81 rather than replacing an extracted or missing tooth and is thus referred to as an "inpontic" dental assembly. The inpontic dental assembly 80 comprises a dental assembly housing 82. The dental assembly housing has an opposed pair of end faces or surfaces 84 and 86 as well as a bottom surface 88 and a circilinear surface 90, preferably having beveled edges wherein it adjoins either end face. The housing 82 has a passageway or axial bore 92 in which is positioned a straight wire transmission pH electrode assembly 50 such that the sensing tip end thereof is proximate one end of the passageway and is preferably recessed as depicted in FIG. 6. Typically, an adhesive, e.g., dental cement is required to secure the pH electrode assembly within the passageway. Such an inpontic dental assembly can have the bottom surface 88 removably attached to either a buccal or lingual facial tooth surface such as by conventional dental ligature wire and/or with coventional acid-etch composite restorative material. It is apparent that such a structure has utility for use in human or animal subjects possessing their full complement of teeth.

While the foregoing description has specifically described wire transmission assemblies having a micro pH indicator electrode (i.e. responsive to hydrogen ion acitvity) it is, of course, to be appreciated that the present invention can be used to prepare assemblies for wire transmission equipped with indicator electrodes responsive to, or other means for measuring, the ionic activity of other ions. For example, micro assemblies for wire transmission having micro electrodes responsive to either fluoride or calcium ionic activity are also useful for dental research. Moisture and ionic migration can also interfere with the continuous and accurate measurement of fluoride or calcium ionic activity by such assemblies. Similarly, the present invention can be used to provide pontic and inpontic dental assemblies containing micro fluoride electrode assemblies for wire transmission.

What is claimed is:

1. A dental assembly useful for the wire transmission measurement of oral cavity fluids' ionic changes by attachment to an existing tooth, comprising:
    A. a dental assembly housing, said housing having a bottom, an opposed pair of end faces, a curvilinear surface, and an axial bore having a first aperture on one end face and a second aperture on the other end face;
    B. an ionic indicator electrode assembly comprising:
        a tubular housing having a first and a second opposed pair of open ends and wherein the housing is of heat shrunken material;
        a cylindrical indicator electrode which is responsive to changes in ionic activity, said indicator electrode including an electrode stem and wherein the electrode is positioned within the tubular housing proximate the first end of the tubular housing defining an annular space therebetween;
        a first means for sealing the electrode to the tubular housing against moisture migration;
        an electrically conductive cylindrical plug positioned proximate the second end of the tubular housing, said plug having a means for electrically connecting the transmission wire to the plug;
        a second means for sealing the plug to the tubular housing against moisture migration;
        a third means for sealing the transmission wire to the plug against moisture migration;
        a means for electrically connecting the indicator electrode to the plug;
    wherein the ionic indicator electrode assembly is positioned within the axial bore such that the first end of the housing is proximate the aperture of one end face; and;
        a means for fixedly attaching the dental housing to the tooth.

2. The dental assembly of claim 1 wherein the indicator electrode is a pH electrode.

3. The dental assembly of claim 2 wherein the first sealing means comprises a sealing layer filling the annular space intermediate the indicator electrode and the tubular housing, said sealing layer comprising a moisture and ionic impermeable, plastic material.

4. The dental assembly of claim 3 wherein the second sealing means comprises a sealing layer filling the annular space intermediate the plug and the tubular housing, said sealing layer comprising a moisture and ionic impermeable, plastic material.

5. The dental assembly of claim 4 wherein the cylindrical plug has a flat facing at one end and wherein the means for electrically connecting includes a socket in the plug opposing the flat facing said socket having a tapered cavity for receiving the transmission wire having a tapered tip.

6. The dental assembly of claim 5 wherein the plug is recessed from the open second end of the tubular housing.

7. The dental assembly of claim 6 wherein the indicator electrode is positioned within the first end of the tubular housing with both the tubular housing and the sealing layer extending outwardly beyond the connection between the sensing tip and the glass cylindrical housing.

8. The dental assembly of claim 7 wherein the means for electrically connecting the electrode to the plug comprises an electrically conductive wire electrically bonded at one end to the electrode stem and electrically bonded at the other end to the flat facing of the plug.

9. The dental assembly of claim 8 wherein the tubular housing has a second end portion extending outwardly beyond the connection between the socket and the transmission wire tip.

10. The dental assembly of claim 9 wherein the third means for sealing the transmission wire to the socket comprises a sealing layer filling the region proximate to the socket and the transmission wire tip, said sealant layer comprising a moisture and ionic impermeable, plastic material.

11. The dental assembly of claim 10 wherein the tubular housing has a first portion proximate the indicator electrode, a second portion proximate the plug and a center portion intermediate the first portion and the second portion and wherein the diameter of the intermediate portion is relatively smaller than the diameter of at least one end portion.

12. The dental assembly of claim 11 further having a sealant material filling the region inside the tubular housing intermediate the indicator electrode and the plug, said sealant layer comprising a moisture and ionic impermeable, plastic material.

13. The dental assembly of claim 11 wherein the cylindrical plug has a flat facing at one end and wherein the means for electrically receiving includes a socket in the plug, said socket having a tapered cavity for receiving the transmission wire having a tapered tip.

14. The dental assembly of claim 13 wherein the exterior aperture of the first passageway is flared.

15. The dental assembly of claim 14 wherein the plug is recessed from the open second end of the tubular housing.

16. The dental assembly of claim 13 wherein the indicator electrode is positioned within the first end of the tubular housing with both the tubular housing and the sealing layer extend outwardly beyond the seam between the sensing tip and the glass cylindrical housing.

17. The dental assembly of claim 15 wherein the means for electrically connecting the electrode to the plug comprises an electrically conductive wire electrically bonded at one end to the electrode stem and electrically bonded at the other end to the flat facing of the plug.

18. A dental assembly for the measurement of oral cavity fluids' ionic changes by connection with a transmission wire by insertion into the abscess between a pair of unextracted teeth remaining from a missing tooth, comprising:
   A. a dental assembly housing having a bottom surface, a top surface, a plurality of sidewalls; a first passageway in a sidewall and a second passageway in a sidewall; and
   B. an ionic indicator electrode assembly, comprising:
      a tubular housing having a first and a second opposed pair of open ends wherein the housing is of heat shrunken material;
      a cylindrical indicator electrode which is responsive to changes in ionic activity, said indicator electrode including an electrode stem, and wherein the electrode is positioned within the tubular housing proximate the first end of the tubular housing defining an annular space therebetween;
      a first means for sealing the electrode to the tubular housing against moisture migration;
      an electrically conductive cylindrical plug positioned proximate the second end of the tubular housing; said plug having a means for electrically connecting the transmission wire to the plug;
      a second means for sealing the plug to the tubular housing against moisture migration;
      a third means for sealing the transmission wire to the socket against moisture migration;
      a means for electrically connecting the indicator electrode to the plug; and
      wherein the ionic indicator electrode assembly is positioned within the housing with the first end of the tubular housing terminating proximate the exterior aperture of the first passageway and the second end of the tubular housing terminating proximate the exterior aperture of the second passageway; and
      securing means for anchoring the electrode assembly within the housing.

19. The dental assembly of claim 18 wherein the first passageway and the second passageway are each located in the same sidewall.

20. The dental assembly of claim 19 wherein the dental assembly housing is in the shape of a tooth.

21. The dental assembly of claim 20 wherein the exterior aperture of the first passageway is flared.

22. The dental assembly of claim 19 wherein the sidewall having the first and the second passageways is thicker than the other sidewalls.

23. The dental assembly of claim 22 wherein the indicator electrode is a pH electrode.

24. The dental assembly of claim 23 wherein the first sealing means comprises a sealing layer filling the annular space intermediate the indicator electrode and the tubular housing, said sealing layer comprising a moisture and ionic impermeable, hydrophobic, plastic material.

25. The dental assembly of claim 24 wherein the second sealing means comprises a sealing layer filling the annular space intermediate the plug and the tubular housing, said sealing layer comprising a moisture and ionic impermeable, hydrophobic, plastic material.

26. The dental assembly of claim 25 wherein the tubular housing has a second end portion extending outwardly beyond the connection between the socket and the transmission wire tip.

27. The dental assembly of claim 26 wherein the tubular housing has a first portion proximate the indicator electrode, a second portion proximate the plug and a center portion intermediate the first portion and the second portion and wherein the diameter of the intermediate portion is relatively smaller than the diameter of at least one end portion.

28. The dental assembly of claim 27 further comprising a sealant material filling the region inside the tubular housing intermediate the indicator electrode and the plug.

29. The dental assembly of claim 28 wherein the third means for sealing the transmission wire to the socket comprises a sealing layer filling the region proximate to the socket and the transmission wire tip, said sealant layer comprising a moisture and ionic impermeable, plastic material.

30. The dental assembly of claim 29 wherein the dental assembly is fabricated from a ceramic material.

* * * * *